United States Patent
Molitor et al.

(10) Patent No.: US 9,024,072 B2
(45) Date of Patent: May 5, 2015

(54) PROCESS FOR REDUCTIVE AMINATION OF ALIPHATIC CYANOALDEHYDES TO ALIPHATIC DIAMINES

(75) Inventors: Erich J. Molitor, Midland, MI (US); Daniel A. Hickman, Midland, MI (US); Shawn D. Feist, Midland, MI (US); David C. Molzahn, Midland, MI (US); Stacie Santhany, Auburn, MI (US); Abraham D. Schuitman, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/383,596

(22) PCT Filed: Jul. 30, 2010

(86) PCT No.: PCT/US2010/043932
§ 371 (c)(1),
(2), (4) Date: Jan. 12, 2012

(87) PCT Pub. No.: WO2011/014787
PCT Pub. Date: Feb. 3, 2011

(65) Prior Publication Data
US 2012/0116124 A1 May 10, 2012

Related U.S. Application Data

(60) Provisional application No. 61/230,380, filed on Jul. 31, 2009.

(51) Int. Cl.
*C07C 209/00* (2006.01)
*C07C 209/48* (2006.01)

(52) U.S. Cl.
CPC ........... *C07C 209/48* (2013.01); *C07C 2101/14* (2013.01)

(58) Field of Classification Search
CPC ..................................................... C07C 209/48
See application file for complete search history.

(56) References Cited

U.S. PATENT DOCUMENTS

| 3,143,570 A | 8/1964 | Caldwell et al. |
| 3,427,356 A | 2/1969 | Suessenguth et al. |

(Continued)

FOREIGN PATENT DOCUMENTS

| DE | 19832529 A1 | 1/2000 |
| EP | 0839796 B1 | 6/2002 |

(Continued)

OTHER PUBLICATIONS

EP Office Action dated Nov. 5, 2013; from EP counterpart Application No. 10739812.5.

(Continued)

*Primary Examiner* — Clinton Brooks (57) ABSTRACT

A process for reductive amination of aliphatic cyanoaldehydes to aliphatic diamines comprising (1) providing a mixture of 1,3-cyanocyclohexane carboxaldehyde and/or 1,4-cyanocyclohexane carboxaldehyde; (2) contacting said mixture with a metal carbonate based solid bed or a weak base anion exchange resin bed at a temperature from 15 to 40 ° C. for a period of at least 1 minute; (3) thereby treating said mixture, wherein said treated mixture has a pH in the range of 6 to 9; (4) feeding said treated mixture, hydrogen, and ammonia into a continuous reductive amination reactor system; (6) contacting said treated mixture, hydrogen, and ammonia with each other in the presence of one or more heterogeneous metal based catalyst systems at a temperature from 80 ° C. to 160 ° C. and a pressure from 700 to 3500 psig; (7) thereby producing one or more cycloaliphatic diamines is provided.

2 Claims, 4 Drawing Sheets

(56) References Cited

U.S. PATENT DOCUMENTS

| | | | |
|---|---|---|---|
| 5,041,675 A | 8/1991 | Lukas et al. | |
| 5,055,618 A | 10/1991 | Kampmann et al. | |
| 5,371,293 A | 12/1994 | Takagawa | |
| 5,756,845 A | 5/1998 | Voit et al. | |
| 5,869,653 A | 2/1999 | Johnson et al. | |
| 6,011,179 A | 1/2000 | Haas et al. | |
| 6,252,121 B1 | 6/2001 | Argyropoulos et al. | |
| 6,429,335 B1 | 8/2002 | Kiai | |
| 7,060,857 B2 | 6/2006 | Funke et al. | |
| 2007/0118001 A1 | 5/2007 | Bocquenet et al. | |

FOREIGN PATENT DOCUMENTS

| | | |
|---|---|---|
| FR | 866545 A | 8/1941 |
| WO | 9819991 A1 | 5/1998 |
| WO | 0107382 A3 | 2/2002 |
| WO | 2007031488 A3 | 5/2007 |
| WO | 2008/076795 A1 | 6/2008 |

OTHER PUBLICATIONS

EP Response to Office Action dated Feb. 12, 2014; from EP counterpart Application No. 10739812.5.
Chinese Response to Office Action dated Jan. 24, 2014; from Chinese counterpart Application No. 201080042896.X.
Chinese Office Action dated May 5, 2014; from Chinese counterpart Application No. 201080042896.X.
Instructions to Chinese Office Action dated Jun. 24, 2014; from Chinese counterpart Application No. 201080042896.X.
Response to Chinese Office Action dated Jul. 1, 2014; from Chinese counterpart Application No. 201080042896.X.
Japanese Associate letter dated Sep. 4, 2014 with Japanese Office Action dated Mar. 18, 2014 for counterpart Japanese Application No. 2012-523095, 5 pages.
Japanese Office Action dated Mar. 18, 2014 and Japanese Associate letter dated Sep. 4, 2014 with proposed amendments for counterpart Japanese Application No. 2012-523095, 5 pages.
Response to Chinese Office Action dated Dec. 25, 2014; from Chinese counterpart Application No. 201080042896.X.
Dow Global Technologies LLC U.S Appl. No. 61/230,300.
J. Mol. Catal. A: Chem. 2003, 206, (1-2), 363-370.
Chem. Ind. (Dekker) 2001, 82, (Catalysis of Organic Reactions), 229-239.
In Chem. Ind. (Dekker), 2001; vol. 82, pp. 201-227.
Dow Global Technologies LLC, EP Appln No. 10739812.5 EPO__Form__1219.
PCT/US2010/043932, International Search Report & Written Opinion.
PCT/US2010/043932, International Preliminary Report on Patentability.

PROCESS FOR REDUCTIVE AMINATION OF ALIPHATIC CYANOALDEHYDES TO ALIPHATIC DIAMINES

CROSS-REFERENCE TO RELATED APPLICATIONS

This application is a non-provisional application claiming priority from the U.S. Provisional Patent Application No. 61/230,380, filed on Jul. 31, 2009, entitled "PROCESS FOR REDUCTIVE AMINATION OF CYCLOALIPHATIC CYANOALDEHYDES TO ALIPHATIC DIAMINES," the teachings of which are incorporated by reference herein, as if reproduced in full hereinbelow.

FIELD OF INVENTION

The instant invention relates to a process for reductive amination of aliphatic cyanoaldehydes to aliphatic diamines, and aliphatic diamines produced via such method.

BACKGROUND OF THE INVENTION

Bis(aminomethyl)cyclohexane is a diamine that has applications as a precursor to an aliphatic diisocyanate (bis(isocyanatomethyl)cyclohexane). It is useful as a chain extender in certain polyurethanes systems and can be used as an epoxy curing agent. Bis(aminomethyl)cyclohexane exists as a number of isomers, of which the 1,3- and 1,4-isomers are of primary interest. The 1,3- and 1,4-isomers can also exist in a number of diastereomeric forms, as the aminomethyl groups can each reside above or below the plane of the cyclohexane ring.

1,3- and 1,4-bis(aminomethyl)cyclohexane mixtures can be prepared via a number of synthetic routes. U.S. Pat. No. 3,143,570 describes a two-step process that requires preparation and isolation of the intermediate solid iminomethylcyclohexanecarbonitriles in water.

As another example, a route may start with butadiene and acrolein, forming 1,2,3,6-tetrahydrobenzaldehyde in a Diels-Alder reaction. This intermediate is then hydroformylated to add a second aldehyde group and reductively aminated to form the desired diamine. A mixture of isomeric forms of the diamine is obtained, as for example, described in the U.S. Pat. No. 6,252,121.

The reductive amination of hydroformylated 1,2,3,6-tetrahydrobenzaldehyde using a sponge-metal catalyst or nickel on silica gel/alumina as in U.S. Pat. No. 6,252,121, however, tends to produce diamine products in low yields. A significant portion of the starting material forms unwanted by-products and polymeric species. As a result, raw material costs may be high and purification of the crude product can be difficult and expensive. Polymeric by-products often foul the reactor and downstream purification unit operations.

It is sometimes possible to suppress by-product formation in reductive amination reactions by "protecting" (or "blocking") the aldehyde groups with an alkyl amine as, for example, described in the U.S. Pat. Nos. 5,041,675 and 5,055,618. The blocked groups are more resistant to polymerization and other unwanted side reactions. However, this approach requires the use of additional raw materials and introduces additional chemical species into the reaction, which must later be removed from the crude product and recycled. Process yields are still far short of those that are needed to have a highly economical process.

Additionally, the production of 1,3- and 1,4-bis(aminomethyl)cyclohexane via a dialdehyde intermediate may be difficult due to catalyst deactivation that leads to rapidly declining yields. Although more stable catalysts have been identified, these catalysts provide lower yields from the very beginning of operation. In addition, the dialdehyde intermediate route requires a reliable and sufficient supply of acrolein.

In order to overcome these catalyst performance issues and avoid potential future acrolein supply issues, the instant invention provides reductive amination of 1,3- and 1,4-cyanocyclohexane carboxaldehyde (CCA). This intermediate is based on an acrylonitrile feedstock, which is more accessible than acrolein. Simultaneous reduction of the nitrile group and reductive amination of the aldehyde functionality require a specialized catalyst. Traditional nitrile reduction conditions and catalysts are more aggressive than aldehyde reductive amination conditions and catalysts. Thus, catalysts and conditions that are effective for complete reduction of the nitrile group may also have a tendency to reduce the aldehyde to the corresponding alcohol, resulting in a yield loss. On the other hand, catalysts and conditions that are typically chosen for reductive amination of an aldehyde are typically ineffective in providing complete reduction of the nitrile group, resulting in yield losses to the intermediate aminonitriles. Additionally, the relatively short lifetime of current catalysts introduces other challenges. Catalysts providing good yields to the diamine product (1,3- and 1,4-bis(aminomethyl)cyclohexanes) consistently lose their activity for the nitrile hydrogenation step within less than 250 hours of time on stream. Economically viable catalysts for this process require a much higher number of hours of lifetime, or, equivalently, pounds of 1,3- and 1,4-bis(aminomethyl)cyclohexanes produced per pound of catalyst.

Accordingly, it would be desirable to provide a method by which cycloaliphatic bis(aminomethyl) compounds can be prepared economically and in high yield.

SUMMARY OF THE INVENTION

The instant invention provides a process for reductive amination of aliphatic cyanoaldehydes to aliphatic diamines, and aliphatic diamines produced via such method.

In one embodiment, the instant invention provides a process for reductive amination of aliphatic cyanoaldehydes to aliphatic diamines comprising the steps of: (1) providing a mixture of one or more cycloaliphatic cyanoaldehydes, optionally water, and optionally one or more solvents, wherein said one or more cycloaliphatic cyanoaldehydes are selected from the group consisting of 1,3-cyanocyclohexane carboxaldehyde, 1,4-cyanocyclohexane carboxaldehyde, mixtures thereof, and combinations thereof; (2) contacting said mixture with a metal carbonate based solid bed or a weak base anion exchange resin bed at a temperature in the range of 15 to 40° C. for a period of at least 1 minute or more, for example 5 minutes or more; (3) thereby treating said mixture, wherein said treated mixture has a pH in the range of 6 to 9; (4) feeding said treated mixture, hydrogen, and ammonia into a continuous reductive amination reactor system; (6) contacting said treated mixture, hydrogen, and ammonia with each other in the presence of one or more heterogeneous metal based catalyst systems at a temperature in the range of from 80° C. to about 160° C. and a pressure in the range of from 700 to 3500 psig; (7) thereby producing one or more cycloaliphatic diamines, wherein said one or more cycloaliphatic diamines are diamines selected from the group consisting of 1,3-bis(aminomethyl)cyclohexane, 1,4-bis(aminomethyl)cyclohexane, combinations thereof, and mixtures thereof.

In an alternative embodiment, the instant invention provides a process for reductive amination of aliphatic cyanoaldehydes to aliphatic diamines comprising the steps of: (1) providing a mixture of one or more cycloaliphatic cyanoaldehydes, optionally water, and optionally one or more solvents, wherein said one or more cycloaliphatic cyanoaldehydes are selected from the group consisting of 1,3-cyanocyclohexane carboxaldehyde, 1,4-cyanocyclohexane carboxaldehyde, mixtures thereof, and combinations thereof; (2) contacting said mixture with a metal carbonate based solid bed or a weak base anion exchange resin bed at a temperature in the range of 15 to 40° C. for a period of at least 1 minute or more, for example 5 minutes or more; (3) thereby treating said mixture; (4) neutralizing said treated mixture, wherein said neutralized treated mixture has a pH in the range of 6 to 9; (5) feeding said neutralized treated mixture, hydrogen, and ammonia into a continuous reductive amination reactor system; (6) contacting said neutralized treated mixture, hydrogen, and ammonia with each other in the presence of one or more heterogeneous metal based catalyst systems at a temperature in the range of from 80° C. to about 160° C. and a pressure in the range of from 700 to 3500 psig; (7) thereby producing one or more cycloaliphatic diamines, wherein said one or more cycloaliphatic diamines are diamines selected from the group consisting of 1,3-bis(aminomethyl)cyclohexane, 1,4-bis(aminomethyl)cyclohexane, combinations thereof, and mixtures thereof.

In an alternative embodiment, the instant invention further provides a cycloaliphatic diamine produced according to the preceding process.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

DETAILED DESCRIPTION OF THE INVENTION

The instant invention provides a process for reductive amination of aliphatic cyanoaldehydes to aliphatic diamines, and aliphatic diamines produced via such method.

In one embodiment, the instant invention provides a process for reductive amination of aliphatic cyanoaldehydes to aliphatic diamines comprising the steps of: (1) providing a mixture of one or more cycloaliphatic cyanoaldehydes, optionally water, and optionally one or more solvents, wherein said one or more cycloaliphatic cyanoaldehydes are selected from the group consisting of 1,3-cyanocyclohexane carboxaldehyde, 1,4-cyanocyclohexane carboxaldehyde, mixtures thereof, and combinations thereof; (2) contacting said mixture with a metal carbonate based solid bed or a weak base anion exchange resin bed at a temperature in the range of 15 to 40° C. for a period of at least 1 minute or more, for example 5 minutes or more; (3) thereby treating said mixture, wherein said treated mixture has a pH in the range of 6 to 9; (4) feeding said treated mixture, hydrogen, and ammonia into a continuous reductive amination reactor system; (6) contacting said treated mixture, hydrogen, and ammonia with each other in the presence of one or more heterogeneous metal based catalyst systems at a temperature in the range of from 80° C. to about 160° C. and a pressure in the range of from 700 to 3500 psig; (7) thereby producing one or more cycloaliphatic diamines, wherein said one or more cycloaliphatic diamines are diamines selected from the group consisting of 1,3-bis(aminomethyl)cyclohexane, 1,4-bis(aminomethyl)cyclohexane, combinations thereof, and mixtures thereof.

In an alternative embodiment, the instant invention provides a process for reductive amination of aliphatic cyanoaldehydes to aliphatic diamines comprising the steps of: (1) providing a mixture of one or more cycloaliphatic cyanoaldehydes, optionally water and optionally one or more solvents, wherein said one or more cycloaliphatic cyanoaldehydes are selected from the group consisting of 1,3-cyanocyclohexane carboxaldehyde, 1,4-cyanocyclohexane carboxaldehyde, mixtures thereof, and combinations thereof; (2) contacting said mixture with a metal carbonate based solid bed or a weak base anion exchange resin bed at a temperature in the range of 15 to 40° C. for a period of at least 1 minute or more; (3) thereby treating said mixture; (4) neutralizing said treated mixture, wherein said neutralized treated mixture has a pH in the range of 6 to 9; (5) feeding said neutralized treated mixture, hydrogen, and ammonia into a reductive amination reactor system; (6) contacting said neutralized treated mixture, hydrogen, and ammonia with each other in the presence of one or more heterogeneous metal based catalyst systems at a temperature in the range of from 80° C. to about 160° C. and a pressure in the range of from 700 to 3500 psig; (7) thereby producing one or more cycloaliphatic diamines, wherein said one or more cycloaliphatic diamines are diamines selected from the group consisting of 1,3-bis(aminomethyl)cyclohexane, 1,4-bis(aminomethyl)cyclohexane, combinations thereof, and mixtures thereof.

The instant invention further provides cycloaliphatic diamines. The cycloaliphatic diamines according to the instant invention comprise the reductive amination reaction product of a treated feed, which may optionally be further neutralized, as described above comprising cycloaliphatic cyanoaldehydes selected from the group consisting of 3-cyanocyclohexane-1-carboxaldehyde, 4-cyanocyclohexane-1-carboxaldehyde, mixtures thereof, and combinations thereof, hydrogen, and ammonia, fed into a reductive amination reactor system, e.g. one or more continuous reactors, one or more batch reactors, one or more semi-batch reactors, or combinations thereof; wherein the treated feed, which may optionally be further neutralized, feed is contacted with one or more heterogeneous metal based catalyst systems at a temperature in the range of from 80° C. to about 160° C. and a pressure in the range of from 700 to 3500 psig; and wherein one or more cycloaliphatic diamines are formed; and wherein said one or more cycloaliphatic diamines are selected from the group consisting of 1,3-bis(aminomethyl)cyclohexane, 1,4-bis(aminomethyl)cyclohexane, combinations thereof, and mixtures thereof.

The one or more cycloaliphatic cyanoaldehydes may be selected from the group consisting of 3-cyanocyclohexane carboxaldehyde, 4-cyanocyclohexane carboxaldehyde, mixtures thereof, and combinations thereof.

3-cyanocyclohexanecarboxaldehyde, CAS No. 50738-61-9, may have the following structure and formula:

$C_8H_{11}NO$
Mol. Wt.: 137.179

4-cyanocyclohexane carboxaldehyde, CAS No. 18214-33-0, may have the following structure and formula:

$C_8H_{11}NO$
Mol. Wt.: 137.179

The a mixture of one or more cycloaliphatic cyanoaldehydes, optionally water, and optionally one or more solvents, wherein said one or more cycloaliphatic cyanoaldehydes are selected from the group consisting of 1,3-cyanocyclohexane carboxaldehyde, 1,4-cyanocyclohexane carboxaldehyde, mixtures thereof, and combinations thereof, may be contacted with a metal carbonate based solid bed or a weak base anion exchange resin bed at a temperature in the range of greater than 10° C., for example 15 to 40° C., for a period of at least 1 minute or more. Such metal carbonate based solid bed may comprise lithium carbonate, sodium carbonate, potassium carbonate, calcium carbonate, cerium carbonate, manganese carbonate, mixtures thereof, and combinations thereof. Such weak base anion exchange resin bed may comprise DOWEX 66, DOWEX MONOSPHERE 77, DOWEX MARATHON WBA, DOWEX MARATHON WBA-2, DOWEX UPCORE Mono WB-500, XUS 43594.00, DOWEX M-43, XUS 43568.00, AMBERLITE IRA92RF, AMBERLITE IRA 92, or another weak base anion exchange resin, as well as mixtures thereof, and combinations thereof. The treated mixture of one or more cycloaliphatic cyanoaldehydes, optionally water and optionally one or more solvents, wherein said one or more cycloaliphatic cyanoaldehydes are selected from the group consisting of 1,3-cyanocyclohexane carboxaldehyde, 1,4-cyanocyclohexane carboxaldehyde, mixtures thereof, and combinations thereof, may further be neutralized to achieve a pH in the range of 6 to 12, for example, 6 to 9.

The reaction between one or more cycloaliphatic cyanoaldehydes, hydrogen, and ammonia may take place in the presence of one or more heterogeneous metal based catalyst systems at a temperature in the range of from 60° C. to 200° C., for example from 80° C. to about 160° C. or from 90° C. to about 130° C., and a pressure in the range of from 500 to 5000 psig, for example from 700 to 3500 psig or from 1400 to 2500 psig. Such one or more heterogeneous metal based catalyst systems may comprise a metal selected from the group consisting of Co, Ni, Ru, Fe, Cu, Re, Pd, oxides thereof, mixtures thereof, and combinations thereof. Such one or more heterogeneous metal based catalyst systems may comprise a bulk metal catalyst system, sponge-metal catalyst system, supported metal catalyst system, mixtures thereof, or combinations thereof. Such one or more heterogeneous metal based catalyst systems may comprise a bulk Co based catalyst system. In a continuous process, the catalyst lifetime facilitates a weight ratio of the one or more cycloaliphatic diamines to one or more heterogeneous metal based catalyst systems that is greater than 300; for example, greater than 500; or in the alternative greater than 900; or in the alternative greater than 1000. The one or more heterogeneous metal based catalyst systems may further comprise a sponge-metal catalyst. The one or more heterogeneous metal based catalyst systems may further comprise one or more promoters or one or more binding agents or one or more catalyst supports. Such one or more promoters may be selected from the group consisting of alkali metals, and alkaline earth metals. Such one or more binding agents may comprise silicon oxide, aluminum oxide, titanium oxide, zirconium oxide, mixtures thereof, or combinations thereof. Such one or more catalyst supports may comprise silicon oxide, aluminum oxide, titanium oxide, zirconium oxide, mixtures thereof, or combinations thereof. Such one or more heterogeneous metal based catalyst systems are commercially available as Raney Cobalt Catalyst from Grace Davison Catalyst Company, Co-0179T cobalt catalyst from BASF, Co-138E cobalt catalyst from BASF, and G-103 cobalt catalyst from Süd-Chemie.

The one or more heterogeneous metal based catalyst systems may be present in an amount necessary to catalyze the reaction between the one or more cycloaliphatic cyanoaldehydes, hydrogen, and ammonia. For example, the catalyst lifetime facilitates a weight ratio of the cycloaliphatic diamines to the one or more heterogeneous metal based catalyst systems to be greater than 300, for example, greater than 500; or in the alternative, greater than 900; or in the alternative, greater than 1000. In one embodiment, the one or more heterogeneous metal based catalyst systems may, for example, comprise a continuous fixed bed catalyst system.

The space velocity, which is defined as mass of one or more cycloaliphatic cyanoaldehydes mixture per mass of catalyst per hour, is in the range of from 0.1 to 10.0 per hour; for example, from 0.1 to 5.0 per hour; or in the alternative, from 0.1 to 3.0 per hour; or in the alternative, from 0.1 to 2.0 per hour; or in the alternative, from 0.1 to 1.0 per hour; or in the alternative, from 0.3 to 0.8 per hour.

Ammonia is present in excess amount relative to the one or more cycloaliphatic cyanoaldehydes. Ammonia may, for example, be present in a range of 2 to 50 moles per mole of one or more cycloaliphatic cyanoaldehydes; or in the alternative, in a range of 5 to 40 moles per mole of one or more cycloaliphatic cyanoaldehydes; or in the alternative, in a range of 8 to 30 moles per mole of one or more cycloaliphatic cyanoaldehydes. Hydrogen may, for example, be present in a range of 3 to 30 moles per mole of one or more cycloaliphatic cyanoaldehydes; or in the alternative, in a range of 3 to 10 moles per mole of one or more cycloaliphatic cyanoaldehydes; or in the alternative, in a range of 3 to 6 moles per mole of one or more cycloaliphatic cyanoaldehydes.

The reaction between one or more cycloaliphatic cyanoaldehydes, hydrogen, and ammonia may optionally take place in the presence of one or more solvents. Such solvents include, but are not limited to, water; 2-propanol (isopropylalcohol), CAS No. 67-63-0; methanol, CAS No. 67-56-1; t-butanol, CAS No. 75-65-0; and tetrahydrofuran (THF), CAS No. 109-99-9. The feed into the reactor may comprise 0 to 90 percent by weight of one or more solvents, based on the combined weight of one or more cycloaliphatic cyanoaldehydes and the one or more solvents; or in the alternative, 0 to 30 percent by weight of one or more solvents, based on the combined weight of one or more cycloaliphatic cyanoaldehydes and the one or more solvents; or in the alternative, 0 to 10 percent by weight of one or more solvents, based on the combined weight of one or more cycloaliphatic cyanoaldehydes and the one or more solvents.

The reaction between one or more cycloaliphatic cyanoaldehydes, hydrogen, and ammonia may take place in a continuous reductive amination reactor system; or in the alternative, it may take place in a batch reactor system; or in the alternative, it may take place in a semi-batch reactor system. Such reactor systems are generally known to a person of ordinary skill in the art. The continuous reductive amination reactor system, the semi-batch reductive amination reactor system, or the batch reductive amination reactor system may comprise one or more reactors in series, in parallel, or combinations thereof.

The one or more cycloaliphatic diamines produced according to the instant invention may be selected from the group consisting of 1,3-bis(aminomethyl)cyclohexane, 1,4-bis(aminomethyl)cyclohexane, combinations thereof, and mixtures thereof.

1,3-bis(aminomethyl)cyclohexane, CAS No. 2579-20-6, may have the following structure or C$_8$H$_{18}$N$_2$
Mol. Wt.: 142.242

1,4-bis(aminomethyl)cyclohexane, CAS No. 2549-93-1, may have the following structure or formula:

C$_8$H$_{18}$N$_2$
Mol. Wt.: 142.242

Additional byproducts may include 3-(aminomethyl)-cyclohexanecarbonitrile, CAS No. 23083-50-3; 4-(aminomethyl)-cyclohexanecarbonitrile, CAS No. 54898-73-6; 3-azabicyclo[3.3.1]nonane, CAS No. 280-70-6; 3-azabicyclo[3.3.1]non-2-ene, CAS No. 7129-32-0; 7-amino-bicyclo[2.2.1]heptane-1-methanamine; 3-(aminomethyl)-cyclohexanemethanol, CAS No. 925921-54-6; 4-(aminomethyl)-cyclohexanemethanol, CAS No. 1074-62-0.

In a process for producing cycloaliphatic diamines according to the instant invention, one or more cycloaliphatic cyanoaldehydes and optionally one or more solvents are treated and neutralized, as described above, to produce a neutralized treated feed. The neutralized treated feed is introduced with hydrogen and ammonia into a reductive amination reactor system and reacted in the presence of one or more heterogeneous metal based catalyst systems at a temperature in the range of from 80° C. to about 160° C. and a pressure in the range of from 700 to 3500 psig to yield one or more cycloaliphatic diamines.

In one embodiment, the neutralized treated feed is contacted with ammonia first and then the product mixture including the product of the reaction of one or more cycloaliphatic cyanoaldehydes with ammonia is contacted with hydrogen in the presence of one or more heterogeneous metal based catalyst systems.

A product mixture including one or more aliphatic diamines, optionally a portion of the product of the reaction of one or more cycloaliphatic cyanoaldehydes with ammonia, optionally a portion of the ammonia, optionally a portion of the hydrogen, optionally a portion of one or more by-products, optionally a portion of the water, and optionally a portion of the one or more solvents is formed in the one or more reactor systems, as described hereinabove. The product mixture is then removed from the one or more reactor systems, and transferred to one or more distillation column arranged in sequential order. After the product mixture is transferred to one or more distillation columns arranged in sequential order, at least a portion of the ammonia, a portion of the hydrogen, or a mixture thereof is removed from the product mixture via one or more distillation steps. Subsequently, at least a portion of the one or more solvents, if optionally present, and/or water is removed via one or more distillation steps. Subsequently, at least a portion of the product of the reaction of one or more cycloaliphatic cyanoaldehydes with ammonia or one or more by-products is removed via one or more distillation steps, thus separating the one or more aliphatic diamines from the product mixture and converting the one or more cyanoaldehydes to one or more aliphatic diamines. The distillation process is further described in the U.S. provisional patent application with Ser. No. 61/230,300, incorporated herein by reference in its entirety.

The method of improving catalytic lifetime in the production of cycloaliphatic diamines according to the instant invention comprises the steps of (1) providing a mixture of one or more cycloaliphatic cyanoaldehydes, optionally water and optionally one or more solvents, wherein said one or more cycloaliphatic cyanoaldehydes are selected from the group consisting of 1,3-cyanocyclohexane carboxaldehyde, 1,4-cyanocyclohexane carboxaldehyde, mixtures thereof, and combinations thereof; (2) contacting said mixture with a metal carbonate based solid bed or a weak base anion exchange resin bed at a temperature in the range of 15 to 40° C. for a period of at least 1 minute or more; (3) thereby treating said mixture; (4) neutralizing said treated mixture, wherein said neutralized treated mixture has a pH in the range of 6 to 9; (5) feeding said neutralized treated mixture, hydrogen, and ammonia into a reductive amination reactor system; (6) contacting said neutralized treated mixture, hydrogen, and ammonia with each other in the presence of one or more heterogeneous metal based catalyst systems at a temperature in the range of from 80° C. to about 160° C. and a pressure in the range of from 700 to 3500 psig; (7) thereby producing one or more cycloaliphatic diamines, wherein said one or more cycloaliphatic diamines are diamines selected from the group consisting of 1,3-bis(aminomethyl)cyclohexane, 1,4-bis(aminomethyl)cyclohexane, combinations thereof, and mixtures thereof; (8) thereby improving catalytic lifetime in the production of cycloaliphatic diamines.

The one or more cycloaliphatic diamines produced according to the instant invention may be used as a precursor to an aliphatic diisocyanate (bis(isocyanatomethyl)cyclohexane), as a chain extender in certain polyurethanes systems, or as an epoxy curing agent.

EXAMPLES

The following examples illustrate the present invention but are not intended to limit the scope of the invention.

Comparative Example A

Figure 1:
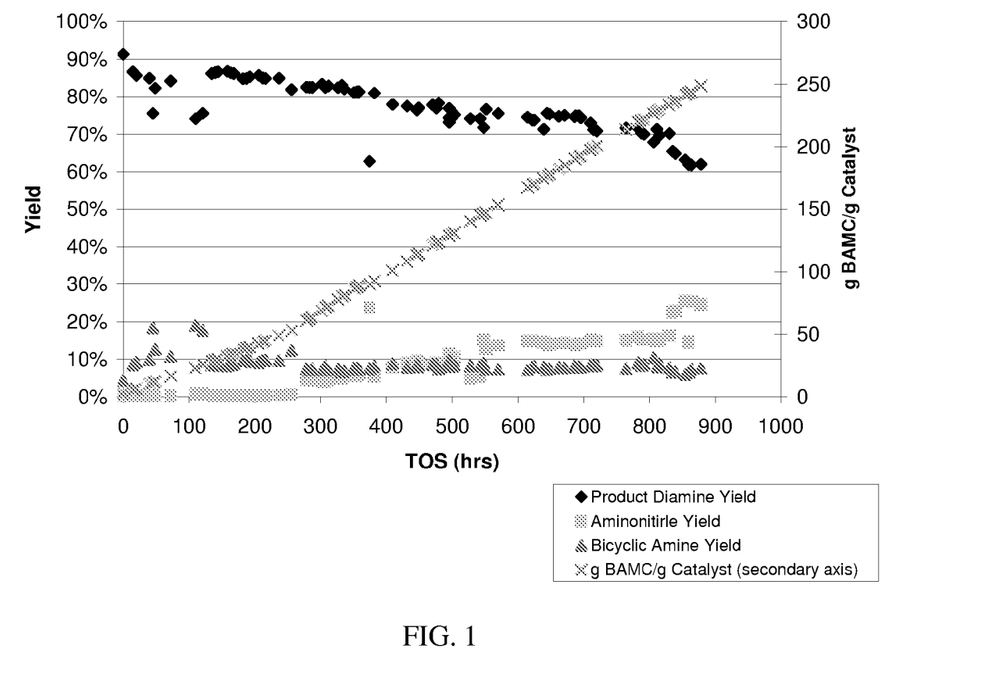
FIG. 1 is a graph illustrating the relationship between diamine product yield and time on stream (TOS) as well as illustrating the relationship between the amount of diamine product yield in grams and the amount of catalyst in grams in the reactor of the Comparative Example A.

A reactor feed mixture was prepared by combining crude cyanoaldehyde, wherein the crude cyanoaldehyde comprises approximately 85 to 90 percent by weight of cyanoaldehyde, with tert-butanol (t-butanol), as solvent, to give a cyanoaldehyde concentration of approximately 22 weight percent. A reactor tube was loaded with 6.7 g of BASF Co-0179T catalyst and diluted with 100 grit (150 µm) SiC (silicon carbide) fines. The temperature of the reactor was raised to 225° C., and the catalyst was activated. The temperature of the reactor was maintained for 14 hours at 225° C., and then it was reduced to a temperature in the range of approximately less than 80° C. under continued hydrogen flow. As soon as the reactor temperature reached below 80° C., an excess flow of ammonia (at about 3 to 5 times the desired set point, as described below) was introduced into the reactor. The temperature and pressure were then changed to the desired set points of approximately 100° C. and approximately 1000 psig. After at least one hour, the rate of the introduction of ammonia into the reactor was decreased to the desired set point of approximately 0.11 mL/min with an organic feed rate of 0.12 mL/min, a liquid hourly space velocity (LHSV, based on combined organic and ammonia volumetric feed rates, (mL Feed/g catalyst/hr)) of 2.0 mL/g/hr with a hydrogen to cyanoaldehyde molar ratio of 7. Samples were periodically collected from the reactor and analyzed by gas chromatography. The flow rates were doubled at 260 hours time on stream (TOS). Yield to product diamine trended down (86.4 percent to 62.0 percent), while aminonitrile yield increased (from 0.07 percent to 24.5 percent) over the initial 850 hours TOS as shown in FIG. 1. The secondary axis in FIG. 1 plots the grams of BAMC (product diamine) produced per gram of catalyst loaded in the reactor. Table 1 reports the cobalt concentration in the reactor effluent in ppm as a function of time on stream.

TABLE 1

| TOS (hours) | Cobalt (ppm) |
| --- | --- |
| 135 | 18.0 |
| 182 | 17.6 |
| 216 | 20.1 |
| 279 | 28.4 |
| 333 | 20.3 |
| 359 | 21.4 |
| 383 | 24.6 |
| 450 | 27.4 |
| 471 | 16.3 |
| 496 | 21.9 |
| 688 | 11.6 |
| 788 | 19.9 |

Inventive Example 1

Figure 2:
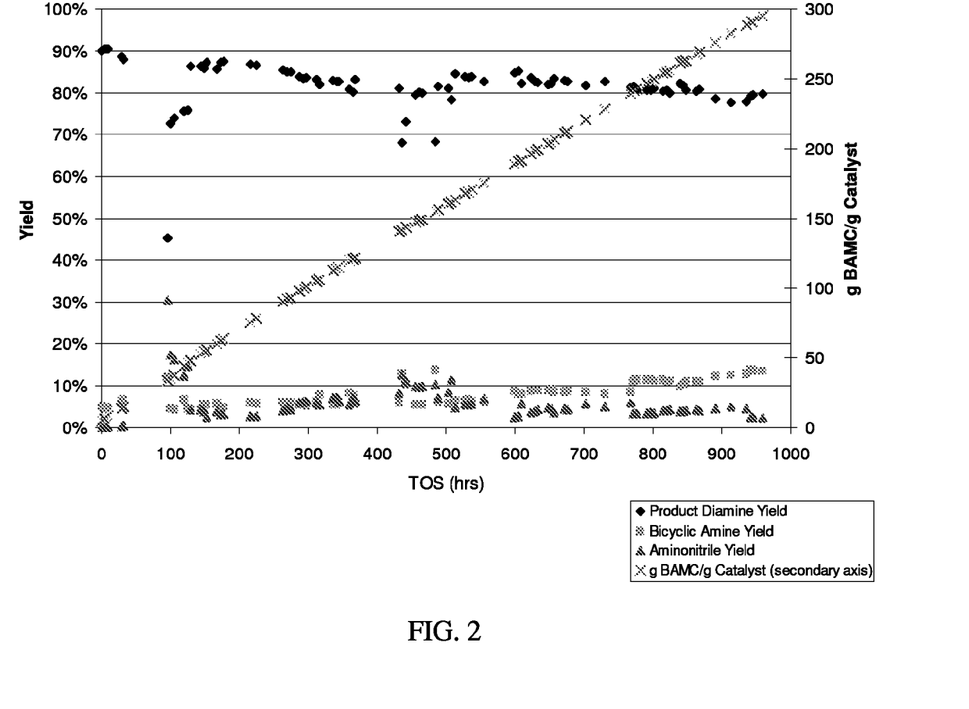
FIG. 2 is a graph illustrating the relationship between diamine product yield and time on stream (TOS) as well as illustrating the relationship between the amount of diamine product yield in grams and the amount of catalyst in grams in the reactor of the Inventive Example 1.

A reactor feed mixture was prepared by combining crude cyanoaldehyde, wherein the crude cyanoaldehyde comprises approximately 85 to 90 percent by weight of cyanoaldehyde, with tert-butanol (t-butanol) to give a cyanoaldehyde concentration of approximately 70 weight percent. The mixture was passed through a bed of sodium carbonate. A reactor tube was loaded with 7.0 g of BASF Co-0179T catalyst and diluted with 100 grit (150 µm) SiC (silicon carbide) fines. The temperature of the reactor was raised to 250° C., and the catalyst was activated. The temperature of the reactor was maintained for 14 hours at 250° C., and then it was reduced to a temperature in the range of approximately less than 80° C. under continued hydrogen flow. As soon as the reactor temperature reached below 80° C., an excess flow of ammonia (at about 3 to 5 times the desired set point, as described below) was introduced into the reactor. The temperature and pressure were then changed to the desired set points of approximately 100° C. and approximately 1400 psig. After at least one hour, the rate of the introduction of ammonia into the reactor was decreased to the desired set point of 0.21 mL/min with an organic feed rate of 0.06 mL/min, a liquid hourly space velocity (LHSV, based on combined organic and ammonia volumetric feed rates, (mL Feed/g catalyst/hr)) of 2.3 mL/g/hr with a hydrogen to cyanoaldehyde molar ratio of 5. Samples were periodically collected from the reactor and analyzed by gas chromatography. The reactor was run for 500 hours at 100° C. The product diamine(1,3- and 1,4-bis(aminomethyl)cyclohexane) yield had been reduced from 90.3 percent to 78.2 percent and the aminonitrile yield increased from 0.06 percent to 11.3 percent. The reactor temperature was ramped to 120° C. to maintain nitrile hydrogenation. The product diamine yield at 960 hours TOS (120° C.) was 79.7 percent as shown in FIG. 2. Bicyclic amine(3-azabicyclo[3.3.1]nonane) yield increased with temperature. The secondary axis in FIG. 2 plots the grams of BAMC (product diamine) produced per gram of catalyst loaded in the reactor versus TOS. Table 2 reports the cobalt concentration in the reactor effluent in ppm as a function of time on stream.

TABLE 2

| TOS (hours) | Cobalt (ppm) |
| --- | --- |
| 1 | 2.7 |
| 337 | 1.4 |
| 600 | 3.1 |

Inventive Example 2

Figure 3:
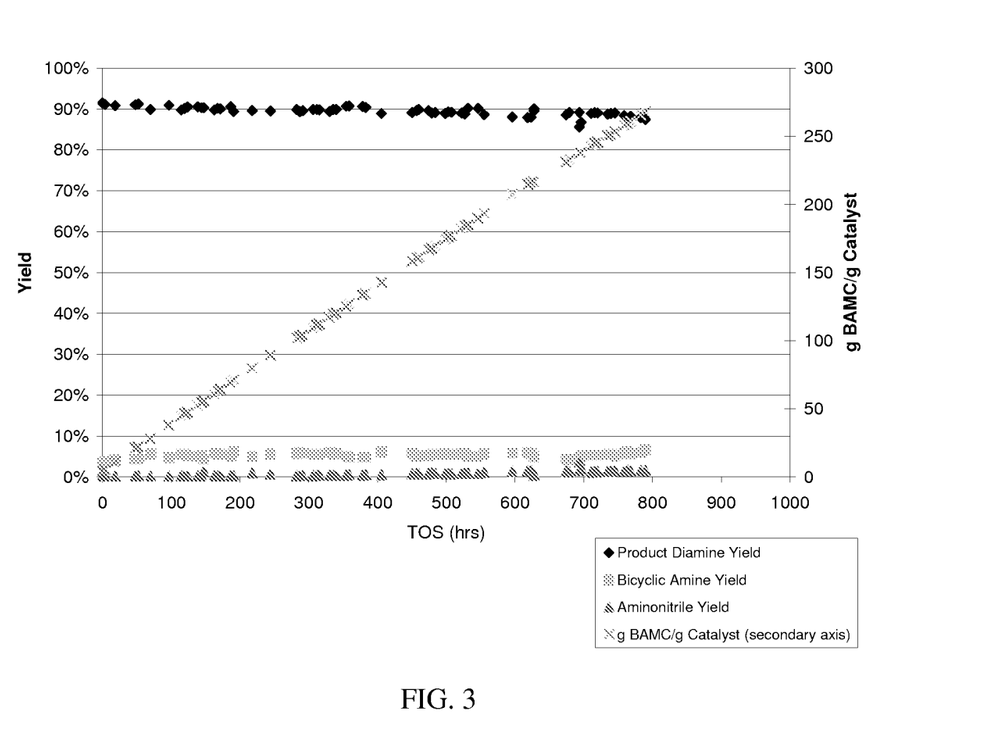
FIG. 3 is a graph illustrating the relationship between diamine product yield and time on stream (TOS) as well as illustrating the relationship between the amount of diamine product yield in grams and the amount of catalyst in grams in the reactor of the Inventive Example 2.

A reactor feed mixture was prepared by combining crude cyanoaldehyde, wherein the crude cyanoaldehyde comprises approximately 85 to 90 percent by weight of cyanoaldehyde, with tert-butanol (t-butanol) to give a cyanoaldehyde concentration of approximately 70 weight percent. The reactor feed mixture was then passed through a bed of lithium carbonate. After the feed was passed through the lithium carbonate bed, water was added to the treated feed. A feed solution with a pH of 6.5-7.0 was obtained. A reactor tube was loaded with 6.6 g BASF Co-0179T catalyst and diluted with 100 grit (150 µm) SiC (silicon carbide) fines. The temperature of the reactor was raised to 250° C., and the catalyst was activated. The temperature of the reactor was maintained for 14 hours at 250° C., and then it was reduced to a temperature in the range of approximately less than 80° C. under continued hydrogen flow. As soon as the reactor temperature reached below 80° C., an excess flow of ammonia (at about 3 to 5 times the desired set point, as described below) was introduced into the reactor. The temperature and pressure were then changed to the desired set points of approximately 100° C. and approximately 1400 psig. After at least one hour, the ammonia rate was decreased to the desired set point of 0.21 mL/min with an organic feed rate of 0.06 mL/min, a liquid hourly space velocity (LHSV, based on combined organic and ammonia volumetric feed rates, (mL Feed/g catalyst/hr)) of 2.4 mL/g/hr with a hydrogen to cyanoaldehyde molar ratio of 6. Samples were periodically collected from the reactor and analyzed by gas chromatography. These conditions were maintained (i.e. no changes in reactor temperature, pressure, or flow rates). Through 800 hours time on stream (TOS) the product diamine (1,3- and 1,4-bis(aminomethyl)cyclohexane) yield had been reduced from 91.1 percent to 87.4 percent and the aminonitrile yield increase from 0.13 percent to 1.51 percent, as shown in FIG. 3. The secondary axis in FIG. 3 plots the grams of BAMC (product diamine) produced per gram of catalyst loaded in the reactor versus TOS. Table 3 reports the cobalt concentration in the reactor effluent in ppm as a function of time on stream.

TABLE 3

| TOS (hours) | Cobalt (ppm) |
|---|---|
| 19 | 14.4 |
| 49 | 19.9 |
| 307 | 15.8 |
| 451 | 5.6 |
| 503 | 4.7 |
| 622 | 5.0 |
| 628 | 5.6 |
| 652 | 4.1 |

Inventive Example 3

Figure 4:
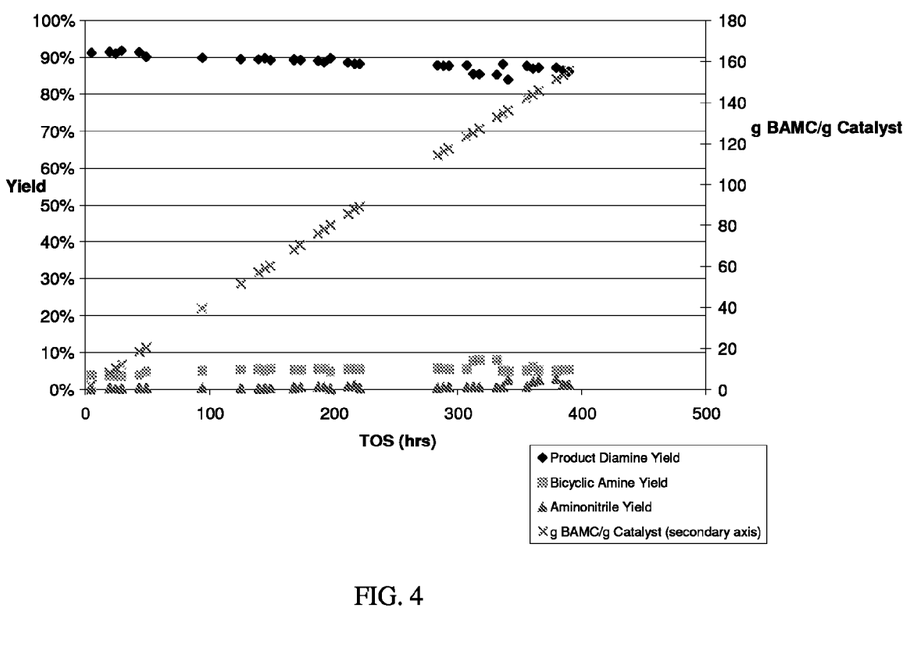
FIG. 4 is a graph illustrating the relationship between diamine product yield and time on stream (TOS) as well as illustrating the relationship between the amount of diamine product yield in grams and the amount of catalyst in grams in the reactor of the Inventive Example 3.

A reactor feed mixture was prepared by combining crude cyanoaldehyde, wherein the crude cyanoaldehyde comprises approximately 85 to 90 percent by weight of cyanoaldehyde, with tert-butanol (t-butanol), and Isonox 132, an antioxidant, to give a cyanoaldehyde concentration of approximately 70 weight percent. The reactor feed mixture was then passed through a bed of DOWEX MONOSPHERE 66. After the feed was passed through the anion exchange resin, a pH of 6.6 was obtained. A reactor tube was loaded with 5.8 g BASF Co-0179T catalyst and diluted with 100 grit (150 µm) SiC (silicon carbide) fines. The temperature of the reactor was raised to 250° C., and the catalyst was activated. The temperature of the reactor was maintained for 15 hours at 250° C., and then it was reduced to a temperature in the range of approximately less than 80° C. under continued hydrogen flow. As soon as the reactor temperature reached below 80° C., an excess flow of ammonia (at least 3 times the desired set point, as described below) was introduced into the reactor. The temperature and pressure were then changed to the desired set points of approximately 100° C. and approximately 1400 psig. After at least one hour, the ammonia rate was decreased to the desired set point of 0.17 mL/min with an organic feed rate of 0.06 mL/min, a liquid hourly space velocity (LHSV, based on combined organic and ammonia volumetric feed rates, (mL Feed/g catalyst/hr)) of 2.3 mL/g/hr with a hydrogen to cyanoaldehyde molar ratio of 4. Samples were periodically collected from the reactor and analyzed by gas chromatography. These conditions were maintained (i.e. no changes in reactor temperature, pressure, or flow rates). Through 389 hours time on stream (TOS) the product diamine (1,3- and 1,4-bis(aminomethyl)cyclohexane) yield had been reduced from 91.5 percent to 86.2 percent and the aminonitrile yield increase from 0.2 percent to 1.3 percent, as shown in FIG. 4. The secondary axis in FIG. 4 plots the grams of BAMC (product diamine) produced per gram of catalyst loaded in the reactor versus TOS. Table 4 reports the cobalt concentration in the reactor effluent in ppm as a function of time on stream.

TABLE 4

| TOS (hours) | Cobalt (ppm) |
|---|---|
| 380 | 3.0 |

The present invention may be embodied in other forms without departing from the spirit and the essential attributes thereof, and, accordingly, reference should be made to the appended claims, rather than to the foregoing specification, as indicating the scope of the invention.

We claim:

1. A process for reductive amination of aliphatic cyanoaldehydes to aliphatic diamines comprising: providing a mixture of one or more cycloaliphatic cyanoaldehydes, optionally water and optionally one or more solvents, wherein said one or more cycloaliphatic cyanoaldehydes are selected from the group consisting of 1,3-cyanocyclohexane carboxaldehyde, 1,4-cyanocyclohexane carboxaldehyde, mixtures thereof, and combinations thereof; contacting said mixture with a metal carbonate based solid bed or a weak base anion exchange resin bed at a temperature in the range of 15 to 40° C. for a period of at least 1 minute or more; thereby treating said mixture; neutralizing said treated mixture, wherein said neutralized treated mixture has a pH in the range of 6 to 9; feeding said neutralized treated mixture, hydrogen, and ammonia into a continuous reductive amination reactor system; contacting said neutralized treated mixture, hydrogen, and ammonia with each other in the presence of one or more heterogeneous metal based catalyst systems at a temperature in the range of from 80° C. to 160° C. and a pressure in the range of from 700 to 3500 psig; thereby producing one or more cycloaliphatic diamines, wherein said one or more cycloaliphatic diamines are diamines selected from the group consisting of 1,3-bis(aminomethyl)cyclohexane, 1,4-bis (aminomethyl)cyclohexane, combinations thereof, and mixtures thereof
wherein said process has a space velocity in the range of 0.1 to 10.0 per hour, and wherein the weight ratio of the cycloaliphatic diamines to one or more heterogeneous metal based catalyst systems is greater than 500.

2. A process for reductive amination of aliphatic cyanoaldehydes to aliphatic diamines comprising: providing a mixture of one or more cycloaliphatic cyanoaldehydes, optionally water, and optionally one or more solvents, wherein said one or more cycloaliphatic cyanoaldehydes are selected from the group consisting of 1,3-cyanocyclohexane carboxaldehyde, 1,4-cyanocyclohexane carboxaldehyde, mixtures thereof, and combinations thereof; contacting said mixture with a metal carbonate based solid bed or a weak base anion exchange resin bed at a temperature in the range of 15 to 40 ° C. for a period of at least 1 minute or more; thereby treating said mixture, wherein said treated mixture has a pH in the range of 6 to 9; feeding said treated mixture, hydrogen, and ammonia into a continuous reductive amination reactor system; contacting said treated mixture, hydrogen, and ammonia with each other in the presence of one or more heterogeneous metal based catalyst systems at a temperature in the range of from 80 ° C. to 160 ° C. and a pressure in the range of from 700 to 3500 psig; thereby producing one or more cycloaliphatic diamines, wherein said one or more cycloaliphatic diamines are diamines selected from the group consisting of 1,3-bis (aminomethyl)cyclohexane, 1,4-bis(aminomethyl)cyclohexane, combinations thereof, and mixtures thereof
wherein said process has a space velocity in the range of 0.1 to 10.0 per hour, and wherein the weight ratio of the cycloaliphatic diamines to one or more heterogeneous metal based catalyst systems is greater than 500.

* * * * *